United States Patent [19]

Pasky

[11] 4,444,985
[45] Apr. 24, 1984

[54] OLIGOMERIZATION OF PROPYLENE

[75] Inventor: Joseph Z. Pasky, Novato, Calif.

[73] Assignee: Chevron Research Company, San Francisco, Calif.

[21] Appl. No.: 402,489

[22] Filed: Jul. 27, 1982

[51] Int. Cl.$^3$ ............................................. C07C 2/02
[52] U.S. Cl. .................................................. 585/520
[58] Field of Search ....................................... 585/520

[56] References Cited

U.S. PATENT DOCUMENTS 2,400,520  5/1946  Kuhn .................................. 585/520
2,440,459  4/1948  Bloch ................................. 585/520
2,462,360  2/1949  Carnell .............................. 585/520

Primary Examiner—Curtis R. Davis
Attorney, Agent, or Firm—S. R. La Paglia; T. G. De Jonghe; C. J. Caroli

[57] ABSTRACT

Preparation of propylene oligomers having from 21 to 48 carbon atoms per molecule by a process which comprises (a) contacting propylene in a reaction zone with a hydrogen fluoride catalyst; (b) maintaining the temperature in the reaction zone between about 20° C. and −30° C.; and (c) maintaining the pressure in the reaction zone between about 0 psig and 400 psig.

3 Claims, No Drawings

OLIGOMERIZATION OF PROPYLENE

BACKGROUND OF THE INVENTION

The present invention relates to the manufacture of heavy olefins intended for use in particular as the raw materials for making surface-active products, lubricating compositions, and the like. More specifically, it relates to a process for preparing heavy olefins from propylene. This process is particularly suitable for the manufacture of olefins having from 21 to 48 carbon atoms per molecule.

Several processes are known for making propylene oligomers. These processes consist essentially of subjecting propylene to the action of appropriate catalysts. The average molecular weight of the oligomer depends on the nature of the catalyst and the conditions of temperature and pressure at which the reaction takes place. It is known, for instance, that oligomers having an average carbon chain length of 12 can be obtained by causing propylene to react on a catalyst based on phosphoric acid, at a temperature of 100° C. to 250° C. approximately, at a pressure from 20 to 100 atmospheres, and that oligomers having an average carbon chain length of about 24 carbon atoms can be obtained by polymerizing propylene in the presence of boron trifluoride, at temperatures of the order of 10° C. to 50° C., in the liquid phase.

U.S. Pat. No. 3,932,553 describes the oligomerization of propylene in the presence of a boron trifluoride catalyst and a small amount of an olefinic diene to provide oligomers having about 15 to 21 carbon atoms.

U.S. Pat. No. 4,024,203 describes the oligomerization of lower molecular weight mono alpha olefins utilizing a catalyst composition containing a Bronsted acid, a sulfone, and optionally, a Lewis acid, to provide predominantly dimers and trimers.

U.S. Pat. No. 4,041,098 describes a method of oligomerizing straight-chain alpha olefins having from 3 to 14 carbon atoms with a soluble catalyst system consisting of an aluminum alkyl halide and an organo halide.

SUMMARY OF THE INVENTION

It has now been found that the production of propylene oligomers having from 21 to 48 carbon atoms per molecule can be achieved by a process which comprises (a) contacting propylene in a reaction zone with a hydrogen fluoride catalyst; (b) maintaining the temperature in the reaction zone between about 20° C. and −30° C.; and (c) maintaining the pressure in the reaction zone between about 0 psig and 400 psig. Among other factors, this invention is based on the discovery that propylene could successfully be oligomerized in the presence of hydrogen fluoride to provide high molecular weight ($C_{21}$–$C_{48}$) olefins in high yield and conversions.

The oligomerization reaction is carried out in the presence of a hydrogen fluoride catalyst. Generally, about 1 to 20, and preferably, about 1 to 5, moles of hydrogen fluoride are utilized per mole of propylene. The reaction proceeds to give from about 60% to over 85% conversion to the oligomer product, depending in large part on the time of reaction involved. The average reaction times necessary to obtain the conversions varies from about 1 to 5 hours, the conversion rate increasing generally with time.

The temperature of the reaction is maintained at about 20° C. to about −30° C., preferably about 0° C. to about −15° C. The reaction pressure is maintained at about 0 psig to about 400 psig, preferably about 100 psig to about 200 psig.

The oligomerization of propylene is carried out in the usual suitable reactor. This reactor has to be designed to withstand the pressure used and corrosion by hydrogen fluoride. It must have a stirrer and the necessary means of cooling the reaction mixture and discharging the heat liberated by the reaction. It must finally be provided with the device and the additional means making it possible to incorporate the reagents and to withdraw the products from the reaction.

The raw product of the reaction includes gaseous products which consist essentially of propane, the main impurity of the propylene used as raw material, and of hydrogen fluoride. They are extracted from the raw product of the reaction by using the usual suitable means that are well known to the technician. After being freed from gas, the oligomer obtained still contains fluoride components derived from the hydrogen fluoride. These compounds cam be eliminated by means of the usual processes, such as fractional distillation.

In the process of the present invention, it has been found that the average molecular weight of the olefins formed by the oligomerization of the propylene is higher, other things being equal, the lower the temperature used. The invention makes it possible in particular to prepare oligomers with an average number of carbon atoms per molecule of about 21 to 48, by performing the reaction at a temperature between about 20° C. and −30° C. With regard to product distribution, the average carbon number varied from $C_{48}$ at −30° C. to $C_{27\text{-}30}$ at +10° C. On the average, one propylene unit is added for each 6° C. decrease in temperature. The optimum temperature range for $C_{33\text{-}39}$ oligomer is 0° C. to −15° C.

The following examples are provided to illustrate the invention in accordance with the principles of the invention but are not to be construed as limiting the invention in any way except as indicated by the appended claims.

EXAMPLES

EXAMPLE 1

To a 1000 ml polypropylene bottle equipped with a stirrer, thermowell, condenser, gas inlet tube and sample port, was added 250 ml (12.5 moles) of hydrogen fluoride. The reaction vessel was immersed in an acetone-ice bath. The mixture was rapidly stirred while bubbling propylene into the reactor and maintaining the temperature at about 10° C. Samples were taken for analysis at 1-hour intervals. The results are shown in Table 1.

TABLE 1

| Time, Hours | Conversion to Material > $C_{18}$ | Average Carbon No. |
|---|---|---|
| 1 | 61% | 24 |
| 2 | 70% | 27 |
| 3 | 76% | 30 |
| 4 | 86% | 36 |

EXAMPLE 2

The procedure of Example 1 was followed, except that the reactor temperature was maintained at about 0°

C. Samples were taken for analysis at 1-hour intervals. The results are shown in Table 2.

TABLE 2

| Time, Hours | Conversion to Material > $C_{18}$ | Average Carbon No. |
|---|---|---|
| 1 | 89% | 27 |
| 2 | 89% | 30 |

EXAMPLE 3

The procedure of Example 1 was followed, except that the reactor temperature was maintained at about $-15°$ C. Samples were taken for analysis at 1-hour intervals. The results are shown in Table 3.

TABLE 3

| Time, Hours | Conversion to Material > $C_{18}$ | Average Carbon No. |
|---|---|---|
| 1 | 83% | 30 |
| 2 | 88% | 33 |

TABLE 3-continued

| Time, Hours | Conversion to Material > $C_{18}$ | Average Carbon No. |
|---|---|---|
| 3 | 93% | 39 |

What is claimed is:

1. A process for the preparation of propylene oligomers having from 21 to 48 carbon atoms per molecule which comprises:
   (a) contacting propylene in a reaction zone with a hydrogen fluoride catalyst;
   (b) maintaining the temperature in the reaction zone between about 0° C. and $-150°$ C.; and
   (c) maintaining the pressure in the reaction zone between about 0 psig and 400 psig.

2. A process according to claim 1, wherein the reaction is carried out at a pressure between about 100 psig and 200 psig.

3. A process according to claim 1, wherein the reaction zone reaction conditions are maintained sufficient to yield at least 60% conversion of the propylene to propylene oligomers having from 21 to 48 carbon atoms per molecule, including a temperature between about 0° C. and $-150°$ C. and a pressure between about 0 psig and 400 psig.

* * * * *

UNITED STATES PATENT AND TRADEMARK OFFICE
CERTIFICATE OF CORRECTION

PATENT NO. : 4,444,985
DATED : April 24, 1984
INVENTOR(S) : Joseph Z. Pasky

It is certified that error appears in the above-identified patent and that said Letters Patent is hereby corrected as shown below:

Column 4, line 14, "and $-150°C.$" should read -- and $-15°C.$ --
Column 4, line 25, "and $-150°C.$" should read -- and $-15°C.$ --

Signed and Sealed this

Eleventh Day of September 1984

[SEAL]

Attest:

GERALD J. MOSSINGHOFF

Attesting Officer       Commissioner of Patents and Trademarks